(12) United States Patent
Kantro (10) Patent No.: US 11,627,909 B2
(45) Date of Patent: Apr. 18, 2023

(54) SYSTEM AND METHOD FOR SELF MONITORING FOR RISK FACTORS FOR THE DEVELOPMENT OF FOOT ULCERATIONS IN A POPULATION OF PEOPLE WITH DIABETES

(71) Applicant: Scott Kantro, Pound Ridge, NY (US)

(72) Inventor: Scott Kantro, Pound Ridge, NY (US)

( * ) Notice: Subject to any disclaimer, the term of this patent is extended or adjusted under 35 U.S.C. 154(b) by 291 days.

(21) Appl. No.: 16/923,839

(22) Filed: Jul. 8, 2020

(65) Prior Publication Data

US 2021/0007656 A1 Jan. 14, 2021

Related U.S. Application Data

(60) Provisional application No. 62/871,890, filed on Jul. 9, 2019.

(51) Int. Cl.
*A61B 5/00* (2006.01)
*A61B 5/01* (2006.01)
(Continued)

(52) U.S. Cl.
CPC .............. *A61B 5/447* (2013.01); *A61B 5/002* (2013.01); *A61B 5/0013* (2013.01); *A61B 5/01* (2013.01);
(Continued)

(58) Field of Classification Search
CPC ....... A61B 5/447; A61B 5/0013; A61B 5/002; A61B 5/01; A61B 5/004; A61B 5/0064; A61B 5/015; A61B 5/6891; A61B 5/747; A61B 5/0036; A61B 5/0022; A61B 5/0008; A61B 2562/0271; A61B 2562/0276; A61B 2562/166; G16H 40/67; G16H 80/00; G16H 10/00; G16H 10/20; G16H 10/40; G16H 10/60; G16H 10/65; G16H 15/00; G16H 30/00; G16H 30/20; G16H 30/40; G16H 40/00; G16H 40/20; G16H 40/40; G16H 40/60; G16H 40/63; G16H 50/00; G16H 50/20; G16H 50/30; G16H 50/50; G16H 50/70; G16H 50/80
See application file for complete search history.

(56) References Cited

U.S. PATENT DOCUMENTS

2007/0211355 A1* 9/2007 Dalbo .................. A61B 5/1036
359/871
2008/0077019 A1* 3/2008 Xiao ..................... G06T 7/0012
600/474
(Continued)

Primary Examiner — David J. McCrosky
Assistant Examiner — Nidhi N Patel
(74) Attorney, Agent, or Firm — Sofer & Haroun, LLP (57) ABSTRACT

An arrangement is provided for monitoring the plantar temperature of the foot having a platform with at least two multi-layer temperature sensitive pads that measure the temperature of a sole of a user's feet. The platform has a scanner for scanning the bottom of the user's feet that produces a digital image thereof. A printed circuit board supports remote connectivity to a mobile application that transmits the scanned digital image of the users' feet to the mobile application for storage and delivery to a physician. The arrangement includes the mobile application that provides a series of diagnostic questions and prompts to the user and is configured to transmit data including the scanned images of the user's feet to a physician.

7 Claims, 7 Drawing Sheets

(51) Int. Cl.
  *G16H 80/00* (2018.01)
  *G16H 40/67* (2018.01)
(52) U.S. Cl.
  CPC ............ *G16H 40/67* (2018.01); *G16H 80/00*
    (2018.01); *A61B 2562/0271* (2013.01); *A61B*
          *2562/166* (2013.01)

(56) References Cited

U.S. PATENT DOCUMENTS

| | | | |
|---|---|---|---|
| 2008/0214962 A1* | 9/2008 | Kantro | A61B 5/6829 |
| | | | 600/592 |
| 2011/0245633 A1* | 10/2011 | Goldberg | A61B 5/165 |
| | | | 600/323 |
| 2013/0261496 A1* | 10/2013 | Engler | A61B 5/0077 |
| | | | 600/549 |
| 2017/0116725 A1* | 4/2017 | Stuart | G06T 7/30 |
| 2018/0132730 A1* | 5/2018 | Linders | A61B 5/447 |
| 2019/0313913 A1* | 10/2019 | Fu | G16H 40/67 |

* cited by examiner

SYSTEM AND METHOD FOR SELF MONITORING FOR RISK FACTORS FOR THE DEVELOPMENT OF FOOT ULCERATIONS IN A POPULATION OF PEOPLE WITH DIABETES

RELATED APPLICATION

This application claims the benefit of priority from U.S. Provisional Patent Application No. 62/871,890, filed on Jul. 9, 2019, the entirety of which is incorporated by reference.

GOVERNMENT LICENSE RIGHTS

This invention was made with government support under grant number 1R43DK126592-01A1 awarded by the National Institutes of Health, NATIONAL INSTITUTE OF DIABETES AND DIGESTIVE AND KIDNEY DISEASES. The government has certain rights in the invention.

FIELD OF THE INVENTION

This invention relates to a device for monitoring the bottom of the foot. More particularly, the present invention relates to a device for monitoring the bottom of the foot for elevated temperatures and foot ulceration conditions.

DESCRIPTION OF RELATED ART

Of all the late complications of diabetes, foot ulceration is among the most common and costly. The morbidity and mortality in those with diabetic foot lesions is worse than many forms of cancer, and the cost of diabetic foot ulcers to Medicare was estimated to be $18.7 billion in 2014. For example, in a study led by Boulton in the UK, in a large community population of 10,000, active foot ulcers were reported in 1.7% of persons with diabetes, with an annual incidence of 2.2%. The pathways to diabetic foot ulceration (DFU) are well recognized and studied, with peripheral neuropathy being one of the most important contributory factors. For more detail, Diabetes mellitus affected over 460 million people worldwide in 2019, a number which has almost doubled in the last decade. In the U.S., the number of adults with diabetes is projected to increase from 22.3 million (9.1%) in 2014 to 39.7 million (13.9%) in 2030 and to 60.6 million (17.9%) in 2060.

Foot problems are also the most common complications in persons with diabetes resulting in hospitalization. In addition, 80% of major amputations in people with diabetes are preceded by foot ulceration. One of the most common mechanisms in the development of neuropathic foot ulceration involves a cumulative effect of unrecognized repetitive trauma at pressure points on the sole of the foot over the course of several days resulting in inflammation and subsequent soft tissue breakdown. Patients with neuropathy have lost the 'gift of pain' in their feet which normally protects from insensitive injury. In normal subjects, pain would cause patients to modify their activity long before a wound develops. However, this is lacking in the neuropathic patient with diabetes: thus, ulcer prevention is one of the foci of any amputation prevention program.

For example, unlike other chronic wounds, DFU usually occurs without warning symptoms because of Diabetic Peripheral Neuropathy (DPN)-related loss of sensation in the lower limbs. As such, educational interventions to prevent the development of insensate DFU have been unsuccessful in increasing foot self-care to substitute for sensory loss and minimize the impact of risk factors. Indeed, persons with diabetes, and especially DFU-naïve individuals, have poor understanding and appreciation of their DFU risk resulting in a lack of preventive foot self-care. Educational interventions have failed to demonstrate reductions in the incidence of ulceration. It is recognized that the neuropathic foot heats up prior to ulceration and studies suggest that education together with subsequent patient involvement by self-foot-temperature monitoring can lead to a reduction in recurrent ulcer incidence. These individuals could therefore benefit from educational interventions allowing them to visualize and regularly monitor their DFU risk.

It is increasingly recognized that repetitive stress to the plantar surface of the neuropathic foot results in inflammation, with the foot heating up before it breaks down. Accordingly, recent studies have tested and subsequently proven the hypothesis that self-foot temperature monitoring, followed by appropriate interventions if one foot is significantly warmer than the other, might reduce the incidence of recurrent ulceration.

One prior art approach to prevent ulceration is to provide padded insoles and protective shoes, educate the patient and their family, and provide regular foot inspection by the patient's primary care physician or podiatrist at intervals of 61-days or longer. Studies have not confirmed that such interventions reduce the rates of first or recurrent ulceration. While the patient is educated regarding the need for daily inspection of their feet at home, there are no easy to use tools that drive adherence to this important preventative measure.

In another approach prior art has suggested that using a remote foot temperature monitoring system could be helpful. An asymmetry of 2.2° C. between the two feet of patients with a DFU history can predict 97% of DFU recurrence. Previously, other studies confirmed that self-foot temperature monitoring in those with past DFU that triggered an intervention (if a temperature difference of 2.2° C. was recorded), was associated with a significant reduction in new DFU compared to standard of care.

Figure 1:
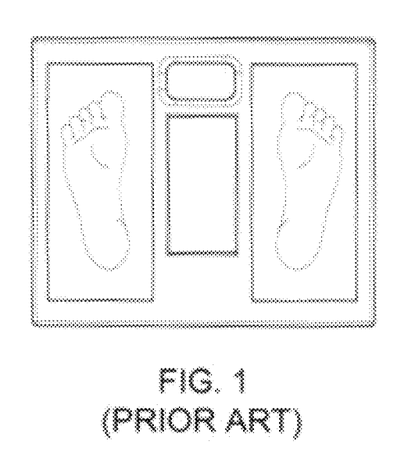
FIG. 1 is a prior art image of a home foot care monitoring device with a mirror.
Figure 2:
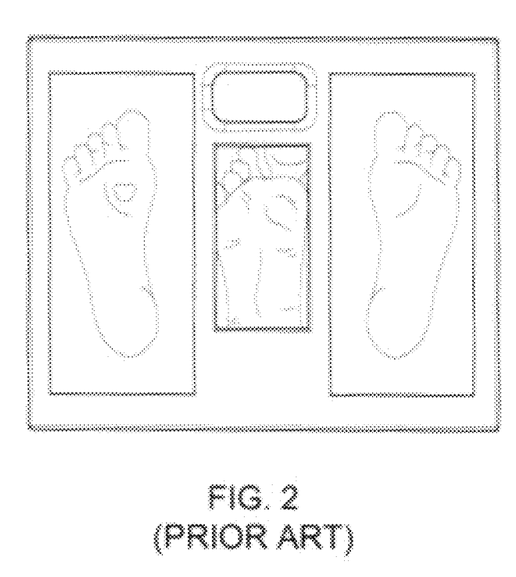
FIG. 2 is a prior art image of the home foot care monitoring device with a mirror of FIG. 1.

One such prior art method to enhance self-monitoring and temperature monitoring is the use of home monitoring temperature pads which includes a temperature monitoring device that could easily be used at home. However, this device relied entirely on the patient to use the device daily and take appropriate preventative action if a 'hotspot' was identified on a foot. See prior art FIG. 1. This home temperature monitoring device uses a liquid crystal technology that produces a thermal image of the feet, allowing identification of areas of elevated temperature on the bottom of the feet, indicating risk of developing a DFU. The device is similar to a bathroom scale as shown in (prior art) FIGS. 1 and 2, permitting easy use: the assessment can be made while sitting comfortably. However, this device currently relies solely on the patient to identify such areas and take appropriate action.

OBJECTS AND SUMMARY

Applicants have developed novel system and method for home monitoring of the temperature of the foot that includes, among other elements, a home-temperature monitoring device that includes a camera or scanner along with a coupled mobile device Application (App) that tracks elevations of skin temperature and the patient's use of the device (date and time of use, results, etc). The application may also be associated with a skin moisture detector in addition to the temperature monitoring device and may prompt the patient for use if the patient is not adherent or if there is an indication of elevated temperature indicating imminent DFU risk by transmitting an alert to the patient's physician for intervention and preventative measures to be implemented.

Such an arrangement as contemplated by the present system and components are intended to be easy to use and will not only alert the patient but also the health care provider as to the imminent DFU risk, should the patient fail to monitor and/or take an appropriate action in response to elevated foot temperature, thereby markedly improving adherence. The system thus may include both a temperature measuring device and a corresponding device that measures skin moisture levels and prompts users to apply lotion which helps to prevent cracking which can lead to infection. A long-handled lotion applicator is also included in the kit, to assist physically challenged patients to apply lotion.

Among the components of the present system, the at-home temperature monitoring device uses liquid crystal thermography (LCT) that provides a thermal image of the feet allowing for easy identification of potential 'hotspots,' or areas of increased temperature suggestive of inflammation. The device is also similar to a bathroom scale, permitting easy use: the assessment can be made while sitting comfortably.

In one embodiment the device is paired with a software Application (App) that tracks skin temperature elevations and will alert the patient and health care professional to the risk of imminent ulceration, thus permitting preventative measures to be initiated. Such tracking arrangement may be contained partly within the temperature/and or moisture measuring device or the related application that tracks and records the data.

To this end an arrangement is provided for monitoring the plantar temperature of the foot. The arrangement includes a device for at home use having a platform. The platform has at least two multi-layer temperature sensitive pads that measure the temperature of a sole of a user's feet. The layers of the temperature sensitive pads provide an overall plantar foot temperature profile for the user's feet.

The platform has a scanner for scanning the bottom of the user's feet, the scanner produces a digital image thereof. A printed circuit board supports remote connectivity to a mobile application that transmits the scanned digital image of the users' feet to the mobile application for storage and delivery to a physician. The arrangement includes the mobile application on an electronic device of the user. The mobile application provides a series of diagnostic questions and prompts to the user, including the use of the multi-layered temperature sensitive pads and the scanner. The mobile application is configured to transmit data including the scanned images of the user's feet to a physician.

BRIEF DESCRIPTION OF THE DRAWINGS

The present invention can be best understood through the following description and accompanying drawing, wherein.

DETAILED DESCRIPTION

Figure 3:
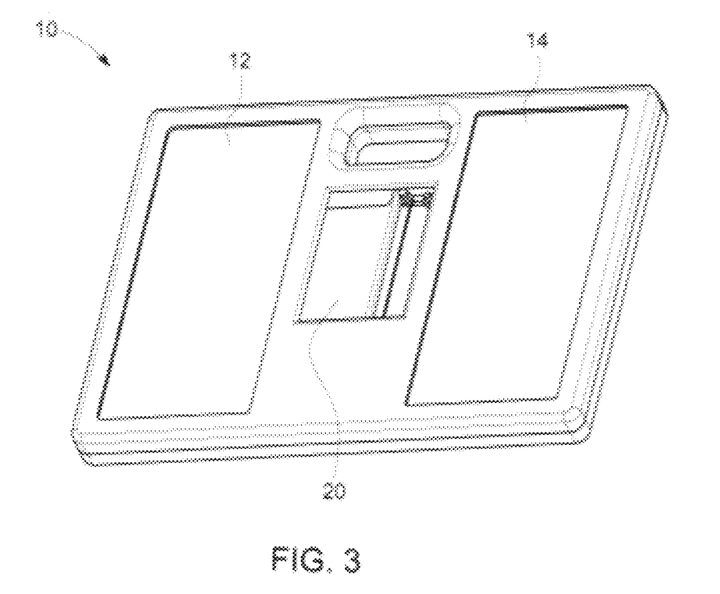
FIG. 3 is home foot care monitoring device with a scanner, in accordance with one embodiment.
Figure 4:
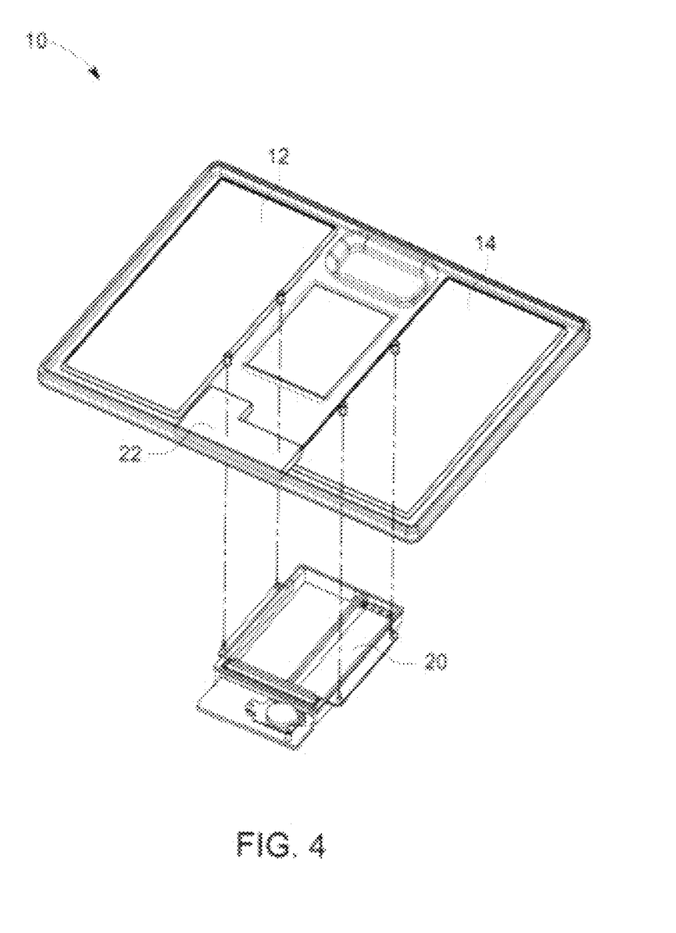
FIG. 4 shows the home foot care monitoring device of FIG. 3 with the scanner element separated, in accordance with one embodiment.

In accordance with one embodiment, as shown in FIGS. 3 and 4, a home monitoring device for the measurement of plantar foot temperature 10 is illustrated with left and right temperature pads 12 and 14 as well as a centrally located scanner 20 and main circuit board 22. FIG. 4 shows the scanner 20, shown separately from device 10.

Regarding temperature pads 12 and 14, such pads may be made of liquid crystals for the purposes of providing the patient a thermal gradient images to help locate 'hotspots' on the bottom of the foot. Each of temperature pads 12 and 14 may be constructed as a multi-layer pad with the layers being sensitive to various temperature ranges that are useful for monitoring the temperature of the foot, and particularly for detecting diabetic conditions. Such a layer structure as described herein is entirely exemplary. Device 10 is understood to be capable of being used in conjunction with temperature pads 12 and 14 of other constructions.

In this exemplary construction for pads 12 and 14, a first layer may be composed of a Chiral Nematic Liquid Crystal due to its expanded temperature range and clearer color imaging. The purpose of the first expanded range was to always obtain a clear, thermal image even in lower temperature environment (approximately 60-70° F.). It was thought that failure to always achieve a thermal image would frustrate the patient and cause him or her to cease using the invention. A Chiral Nematic layer was used for superior imaging at a broader range. A 2° temperature spread per color change was deemed to be sufficient for readings at this temperature range.

A second layer is used to achieve a clear thermal image in the mid-range (approximately 74-80° F.). The purpose of the second layer is to provide a clear thermal image, but as the this mid-range is closer to the norm for a healthy foot, the tolerance between color change events is lowered to approximately 1.5° to enable a clearer differentiation at closer relative temperatures. By compressing the range to a 6° spread, this clearer color differentiation between smaller temperature intervals is achieved.

A third layer may be constructed specifically to identify temperature changes in the neuropathic foot, which has a higher mean foot temperature than a healthy foot. In this layer, the temperature spread is compressed to a 4° F. spread, so that an identifiable color change would in tighter temperature intervals—closer to 1° F. intervals. As the average neuropathic foot temperature is determined to be 82°, this layer is designed to achieve a glow-green color at this normal range so that higher temperature areas (represented by increasingly darker blue colors) would be readily apparent and clearly distinguishable. The purpose of the tighter spread is to enable a more clearly discernible and differentiated color pattern at the higher end of the range so that temperature differentials at the higher end of the range were readily apparent.

A fourth layer may include a leuco dye that is set to clear (and reveal the florescent yellow ink backing) at approximately 88°, because high risk temperature for inflammation is scientifically proven to be between 88 and 90° F. The purpose of the leuco dye is to reveal a clearly distinctive fluorescent pinkish-orange or yellow ink at the highest end of the range so that a very distinctive color differentiation from the contra-lateral footprint is observed.

Such thermal image of the patient's feet normally takes 60+/−5 seconds to fully develop and is dependent upon contact not pressure. Once the patient removes their feet from pads 12 and 14, the thermo-graphic map degrades back to the original appearance at room temperature within minutes. However, the areas indicative of the hottest foot contact temperatures ("Hot Spots") will be clearly discernable compared to adjacent areas of the thermal image of that foot and the same position on the thermal image of the contra-lateral foot. Further, the hottest areas will be the last to degrade and there will be ample time (as much as one minute or more) for the patient or a care giver to note this difference. The leuco indicator is designed to last even longer than the LCT so that the fluorescent yellow spot which appears at the highest temperature range will last the longest. The matt surface of pads 12 and 14 and their Lexon surfaces prevent reflections that would impair photo quality.

Based on the above, when using device 10, and pads 12 and 14 thereon, a patient is able to immediately have an initial impression of areas of concern on the bottom of their feet, even prior to the subsequent steps.

Turning to the other component on device 10, scanner 20 is positioned between pads 12 and 14 to further provide a means to generate a digital image of the bottom of each foot, scanner 20 being supported by the printed circuit board 22 (PCB-22) as shown in FIGS. 3 and 4 Starting with an exemplary construction of scanner 20, such device may include a typical power button to enable the scanner system. Power may be removed automatically when the user completes their scans, or a pre-set time expires. Scanner 20 may include a low power mode when the related application (described below) is not running on a user's mobile device.

In one arrangement, scanner 20 may have a rechargeable battery, possibly with alerts being provided to an accompanying application when the power level drops below a certain power level, with instructions to the user to recharge. Scanner 20 may have a typical colored LED light that will glow from inside the device when charging.

In one arrangement, scanner 20 may include wireless capability and color scanning capabilities. The components thereof can be mounted on and/or connected to printed circuit board (PCB) 22 that provides support and interconnect between the components and a scanner stepper motor. PCB 22 and scanner module 20 may be mounted into the frame of device 10. Some exemplary details of the operation of scanner 20 are detailed below.

In one example, prior to starting their daily foot examination, the patient can check to ensure that the room temperature is within the specified range for use. To accomplish this device 10 may have thermographic ink on the front to indicate the temperature range is acceptable or if the Bluetooth Low Energy (BLE) device in scanner 20 may also include a temperature sensor that alerts the patient via the connected app that the temperature is within proper range.

In one arrangement scanner 20 and PCB 22 use electronic modules to provide regulated power, computing power, wireless capability and 150 dpi or higher color scanning. The components of scanner 20 may be mounted on printed circuit board (PCB) 22 that provides support and interconnection between the components and a scanner stepper motor. PCB 22 and scanner 20 are mounted into the frame of device 10. As noted above, device 10 may include a rechargeable Lithium Ion battery that is recharged through a small power supply that is included and can be charged using any universal micro-USB charger.

Regarding the mechanical operation of device 10, scanner 20, and PCB 22 a Lithium Ion battery and the external power connection can be connected to the charger board through connections on PCB 22. PCB 22 regulates, as required, by a main processor chip and the hardware of scanner 20. When the user presses the power switch, PCB 22 can begin its 'boot sequence' and within a few seconds the user can begin using device 10. Once the processor 'boots' and connects to the mobile device application (app) the user can follow instructions on the app as described in more detail below.

Figure 5:
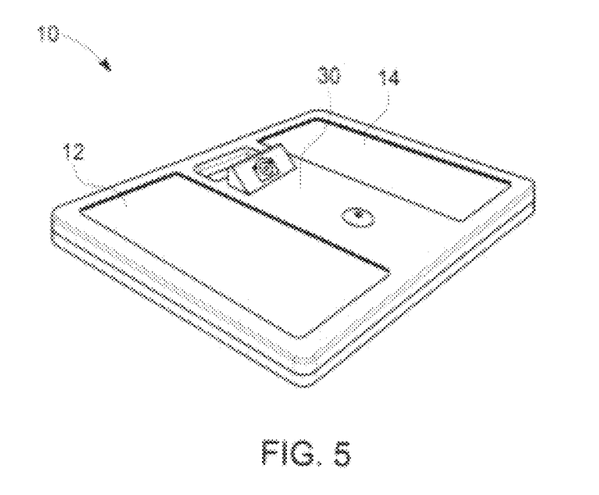
FIG. 5 is home foot care monitoring device with a camera, in accordance with one embodiment.
Figure 6:
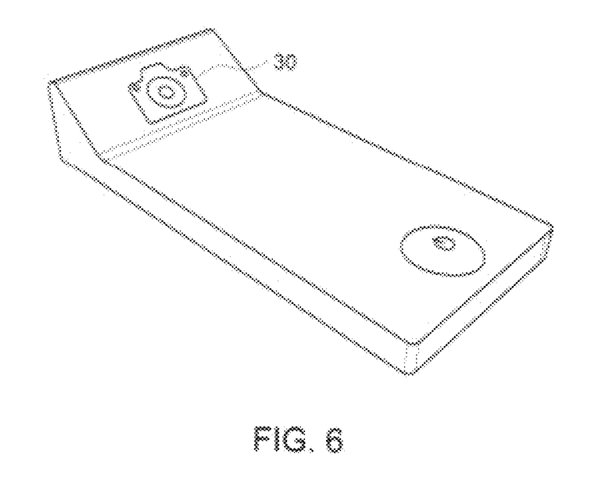
FIG. 6 shows a camera element of the home foot care monitoring device of FIG. 6, in accordance with one embodiment.

It is noted that device 10 may implement a camera 30 instead of a scanner 20 as shown for example in the alternative embodiment shown in FIGS. 5 and 6. In the preferred arrangement, scanner 20 is the imaging device, but the features of this invention may also be implemented with digital camera 30 of sufficient resolution and focus ability.

Figure 7:
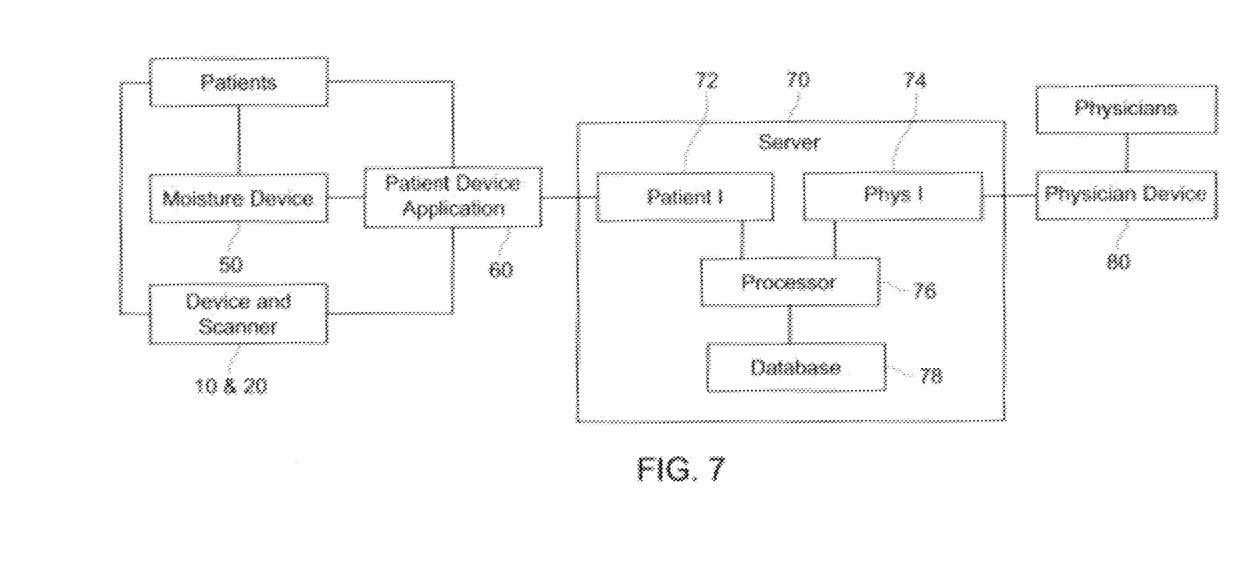
FIG. 7 shows the foot care monitoring device with a scanner, within the context of a larger home monitoring system, in accordance with one embodiment.

Turning to the implementation of device 10 for at home foot temperature monitoring, FIG. 7 shows device in the context of an overall arrangement for patients and doctors to communicate with one another to maintain comprehensive and regular foot temperature monitoring. In one exemplary embodiment, device 10 as shown in FIG. 7 is constructed as outlined above with relationship to FIGS. 3 and 4.

In one embodiment, the present arrangement may further include a moisture monitoring device 50 to be used in conjunction with the foot temperature and scanning device 10. Dry skin is a common dermatological condition and assessment of skin moisture levels of the hands, arms, skin and face has been used extensively for many years in the cosmetics industry. Skin moisture device 50 may be handheld and have a digital display for skin moisture readings on the handle. A neck portion may extend about 9 inches to allow for easy accessibility to the user's feet. Non-invasive probes are located at the distal tip of the neck and are applied to the skin of the feet for approximately 10 seconds to capture a reading. Such a device 50 may be battery powered and could be operated by pressing a button to turn it on which can allow it to pair with application 60 (described below). The readings are sent to the application 60 via Bluetooth Low Energy (BLE) where they are collected.

As shown in FIG. 7, both device 10 and optional skin moisture device 50 are connected to an application 60 via a wireless connection. In one embodiment application 60 is implemented as a mobile application on a user's smart device, such as their smart phone or mobile pad device, but any electronic platform could possibly be used to support such application. The operation of application 60 in connection with device 10 is described in more detail below in the related operation flow chart FIG. 8.

As shown in FIG. 7, a server 70 is implemented within the present arrangement as interfacing with application 60 to collect data from device 10 and moisture device 50 delivered thereto from application 60. Server 70 may include a patient side interface 72, a physician side interface 74, processor 76 and database 78 to implement the various functions of the present system and method. Such elements are considered exemplary and other necessary components may be implemented as well, or such functions combined if desired.

Moreover, server 70 is shown as a stand-alone server potentially supporting a number of connected physicians and patients, however it is understood that such server 70 may also be implemented as an independent functional arrangement within a physicians' office directly. Likewise, such functions and modules of server 70 may be implemented in a cloud-based solution if desired.

Finally, as shown in FIG. 7, the physician would collect and review data as well as interface with the patients via their own device 80, such as desktop computer, laptop, or mobile pad device.

Figure 8:
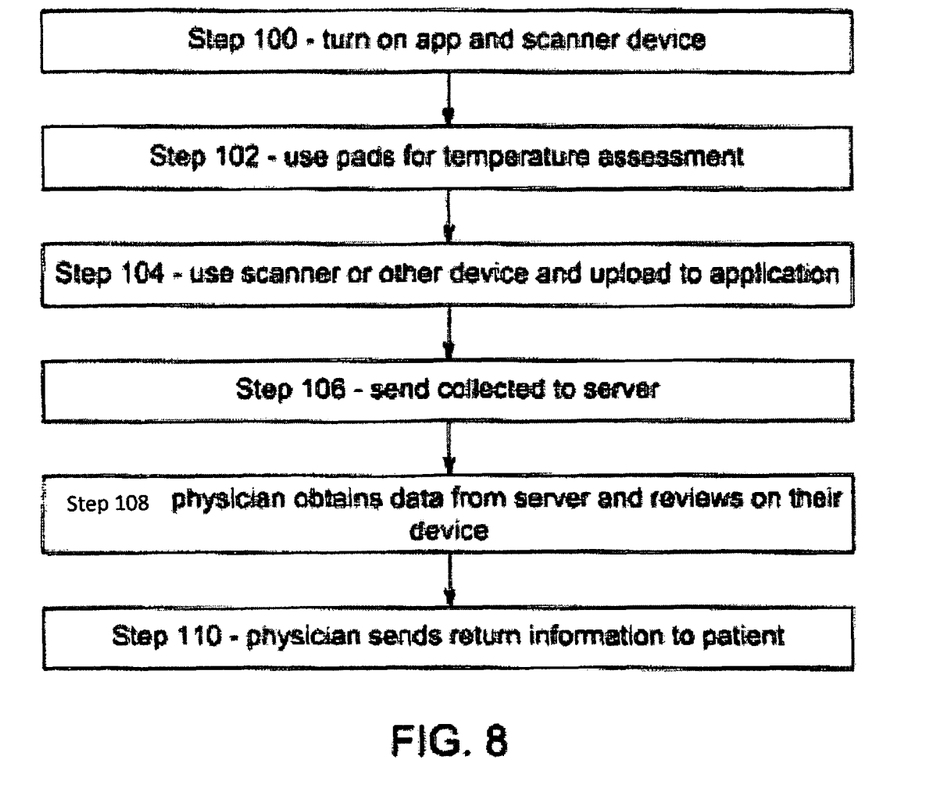
FIG. 8 is a flow chart for the foot care monitoring device with a scanner, within the context of a larger home monitoring system of FIG. 7, in accordance with one embodiment.

In one embodiment of present arrangement, the present system and method is implemented as a series of home monitoring steps as outlined in exemplary flow chart FIG. 8.

At a first step 100 a patient activates device 10 and optional skin moisture measurement device 50 as well as the related application on their mobile device 60. In a preferred implementation such devices are connected wireless via Bluetooth® or other such wireless connectivity arrangement.

At step 100, application 60 asks the patient questions about the condition of their feet, offers interactive feedback and education and then directs patient to step 102, where they place their feet while in a sitting position on liquid crystal pads 12 and 14 of device 10 to obtain their initial color coded reading of their plantar foot temperature, and possible 'hotspots'.

While in use, if the user sees an indicator of a preulcerative condition or wound on the bottom of their foot as indicated by the LCT pads 12 and 14, application 60 can instruct the user to scan the questionable area in a subsequent scanning step 104 using device 10. If a scan is required, the user will place the indicated 'hot spot' area on scanner bed 20 and begin scanning as explained in more detail above. Once the scan is complete, application 60 can display the image to the user on their mobile device via the Bluetooth Low Energy (BLE) connection. If the image quality is not clear, the user may be instructed to retake the scan. The user then selects the image to send to a secure cloud through the app's user interface using Hypertext Transfer Protocol Secure (HTTPS) data transfer.

Such scanning, if directed by application 60, at step 104, via device 10 (using scanner 20 or camera 30) is uploaded to their application 60 for eventual transmission to server 70 and the physician device 80. At this step 104 optional skin moisture measurement device 50 may also use with its data likewise transmitted to application 60.

It is noted that the color temperature pads 20 are not directly connected to application 60 but are more for patient confirmation and to offer immediate feedback. Thus, after step 104, scanned images of the patient's feet as well as the skin moisture data are stored in application 60. Application 60 drives the patient to manually enter any observations from color pads 12 and 14 that may help the physician, such as indicating a 'hotspot' seeing on pads 12 and 14 that does not otherwise appear as an ulceration on the scan images from scanner 20. In the event of a 'hotspot' or other injury noted by the patient in Application 60, the patient will be instructed to contact their health care provider for an appointment for evaluation and management. For example, if a patient responds to a question in application 60 indicating that the patient has seen a 'hotspot', with or without an image, application 60 may generate an alert which is sent to the heath care provider's (HCP) dashboard via an HTTPS data polling process to ensure that the patients makes contact with the physician.

At step 106, once collected, application 60 transmits the collected data and images to server 70 to be stored in database 78 as required. At an appointed time or when alerted, at step 108, the physician can access the patient's scanned image(s) via a secure link to a secure database and view on their device 80 so they can review the patient's scanned image of their feet.

Observations or notes passed along from the patient are delivered via an alert which the physician can review. The physician may then use this home monitoring information to determine if the patient has had any deteriorations/ulcerations, or other serious issues. The physician may also store such patient data to their medical records or transmit such files to patient's primary care physician for example so that all of patient's doctors (e.g. those treating them for diabetes) would have such collected data.

At step 110, once the physician has reviewed the scan and other data, the physician can send an acknowledgement to the patient from their device 80, through server 70 to the patient's device/application 60 indicating that the transmission was properly transmitted, saved and reviewed. With this acknowledgement, the physician can send additional notes to the patient including the schedule for the next home monitoring test, or possibly an alert to call the physician if they spotted an issue that requires a follow up call (or appointment).

Figure 9:
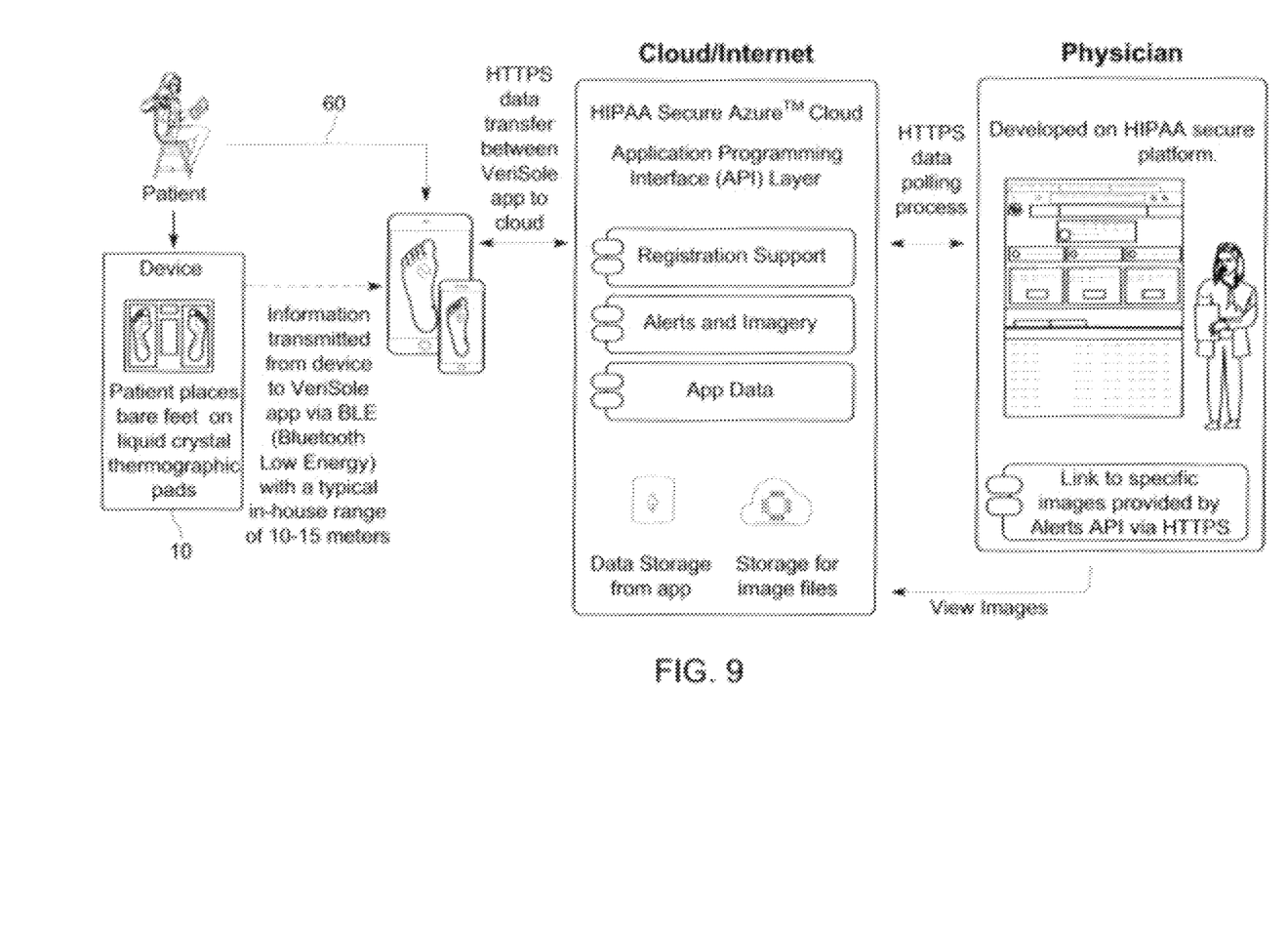
FIG. 9 is an architecture map showing the relative connectivity between the application, device and the physician, in accordance with one embodiment.

A final FIG. 9 is included to provide an overall view of how device 10 and application 60, along with the physician, can use such features described above to ensure adherence to HIPAA rules and regulations. Such illustration of FIG. 9 shows the patient in the context of device 10 and application 60, connected through the cloud/internet/servers to be managed by the physician.

While only certain features of the invention have been illustrated and described herein, many modifications, substitutions, changes or equivalents will now occur to those skilled in the art. It is therefore, to be understood that this application is intended to cover all such modifications and changes that fall within the true spirit of the invention.

What is claimed is:

1. An arrangement for monitoring a plantar temperature of a foot, said arrangement comprising:

a device for at home use having a platform, said platform having at least two multi-layer temperature sensitive pads that measure the temperature of a sole of a user's feet, said at least two multi-layers of said temperature sensitive pads providing an overall plantar foot temperature profile for said user's feet;

said platform also having a scanner for scanning a bottom of a user's foot, said scanner producing a digital image thereof; and a printed circuit board for supporting remote connectivity to a mobile application for transmitting said scanned digital image of said users' feet to said mobile application for storage and delivery to a physician, said arrangement further comprising:

said mobile application on an electronic device of said user, wherein said mobile application is configured to provide a series of diagnostic questions and prompts to said user, including at least one question and prompt indicating, upon detection of a hot spot on their foot, to scan said digital image of said bottom of said user's foot to provide a visual image of said user's foot, and wherein said mobile application is configured to transmit data, including said scanned images of said user's foot to a physician.

2. The arrangement as claimed in claim 1 wherein said at least two multi-layer temperature sensitive pads include a layer of chiral nematic liquid crystal configured to obtain a clear thermal image in the range of 60-70° F.

3. The arrangement as claimed in claim 1 wherein said at least two multi-layer temperature sensitive pads include a cholesteric layer configured to obtain a clear thermal image in the range of 74-80° F.

4. The arrangement as claimed in claim 1 wherein said at least two multi-layer temperature sensitive pads include a cholesteric layer configured to obtain a clear thermal image in the range of 82° F.

5. The arrangement as claimed in claim 1 wherein said at least two multi-layer temperature sensitive pads include a leuco dye layer configured to obtain a clear thermal image in the range of 88° F.

6. The arrangement as claimed in claim 1, wherein said scanner is a wireless scanner connected with a printed circuit board in said device.

7. The arrangement as claimed in claim 1, wherein said mobile application is further connected to a skin moisture detection device, the results of which are combined with said scanner data to be sent to said physician.

* * * * *